United States Patent [19]

Hill et al.

[11] Patent Number: 5,098,439
[45] Date of Patent: Mar. 24, 1992

[54] SMALL INCISION INTRAOCULAR LENS INSERTION APPARATUS

[75] Inventors: Charles M. Hill, Garden Grove; Daniel Brady, Mission Viejo; Timothy R. Willis, Lake Forest; Lyle E. Paul, El Toro, all of Calif.

[73] Assignee: Allergan, Inc., Irvine, Calif.

[21] Appl. No.: 336,876

[22] Filed: Apr. 12, 1989

[51] Int. Cl.⁵ .............................................. A61F 9/00
[52] U.S. Cl. ..................................... 606/107; 623/4
[58] Field of Search ........................ 606/107; 623/4,6

[56] References Cited

U.S. PATENT DOCUMENTS

| | | |
|---|---|---|
| 4,190,049 | 2/1980 | Hager et al. |
| 4,527,294 | 7/1985 | Heslin |
| 4,619,657 | 10/1986 | Keates et al. |
| 4,681,102 | 7/1987 | Bartell |
| 4,699,140 | 10/1987 | Holmes et al. |
| 4,715,373 | 12/1987 | Mazzocco et al. |
| 4,732,150 | 3/1988 | Keener, Jr. |
| 4,747,404 | 5/1988 | Jampel et al. |
| 4,759,359 | 7/1988 | Willis et al. |
| 4,763,650 | 8/1988 | Hauser |
| 4,765,329 | 8/1988 | Cumming et al. |
| 4,769,034 | 9/1988 | Poley |
| 4,781,719 | 11/1988 | Kelman |
| 4,785,810 | 11/1988 | Baccala et al. |
| 4,834,094 | 5/1989 | Patton et al. |
| 4,836,201 | 6/1989 | Patton et al. |
| 4,880,000 | 11/1989 | Holmes et al. |
| 4,919,130 | 4/1990 | Stoy et al. ............ 606/107 |
| 4,934,363 | 6/1990 | Smith et al. .......... 606/107 |

FOREIGN PATENT DOCUMENTS 0363213 4/1990 European Pat. Off.
WO8910729 11/1989 PCT Int'l Appl.

Primary Examiner—C. Fred Rosenbaum
Assistant Examiner—William Lewis
Attorney, Agent, or Firm—Frank J. Uxa, Jr.; Gordon L. Peterson

[57] ABSTRACT

An apparatus for inserting a foldable lens into an eye through an incision in the eye comprising: a paddle permanently affixed to the apparatus, and sized and adapted to contact the lens in the unfolded state; an elongated tube including a distally open interior space sized and adapted to receive the paddle in contact with the lens in the folded state, and a distal end portion sized and adapted to be inserted into the eye through the incision, the tube being cooperable with the paddle to fold the lens into the folded state as the lens in contact with the paddle is received through the distal opening into the interior space; and a mechanism to provide relative movement between the paddle and the tube.

15 Claims, 4 Drawing Sheets

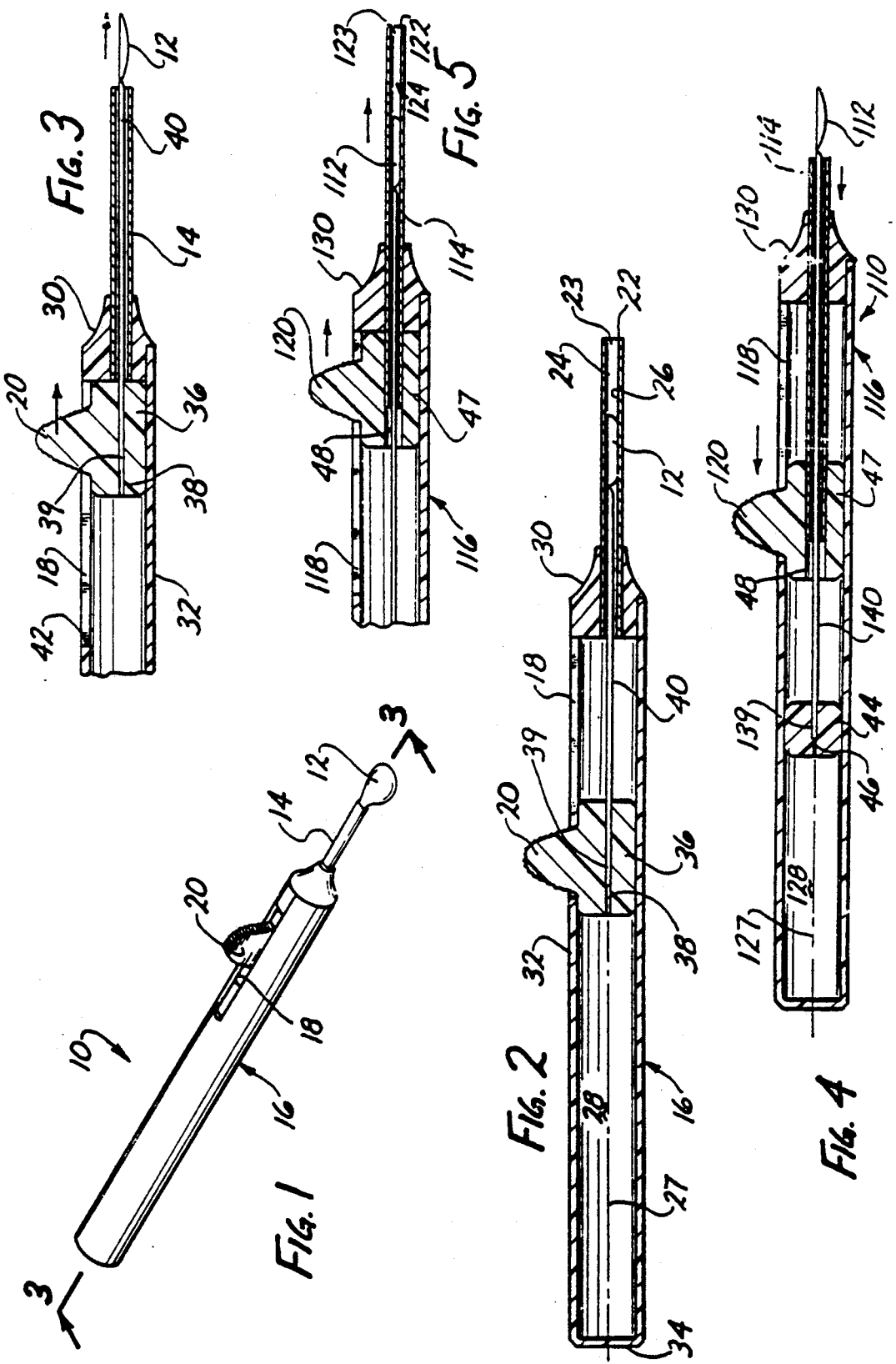

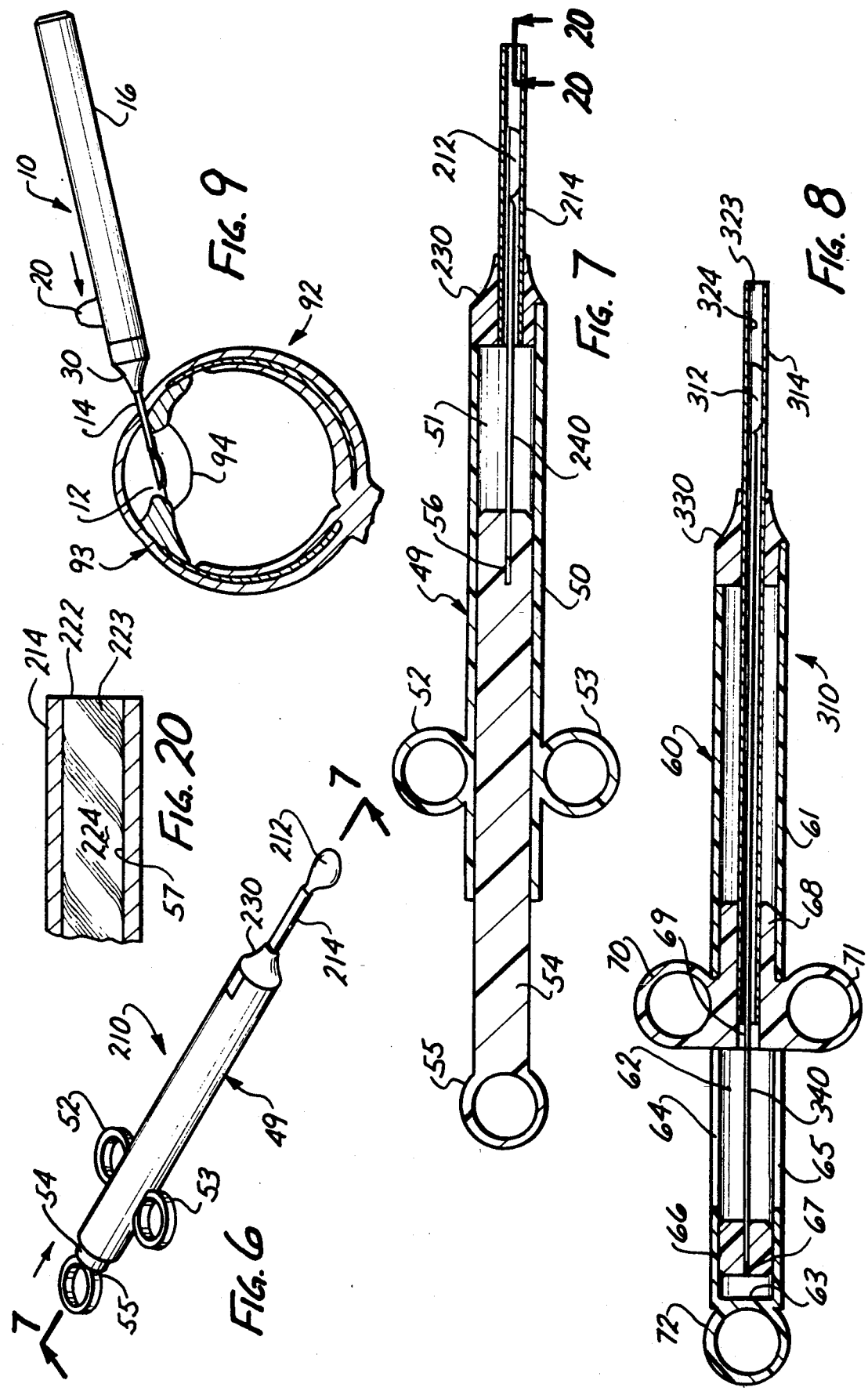

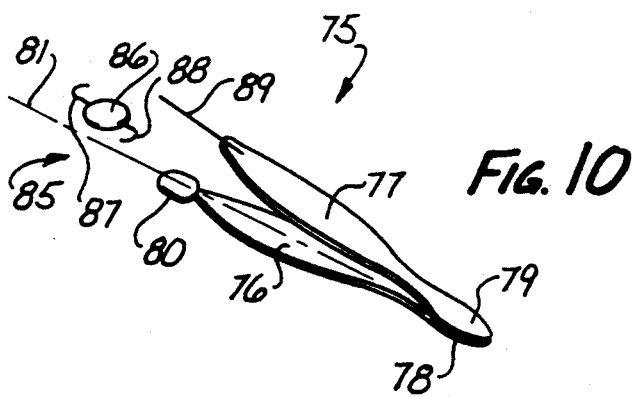
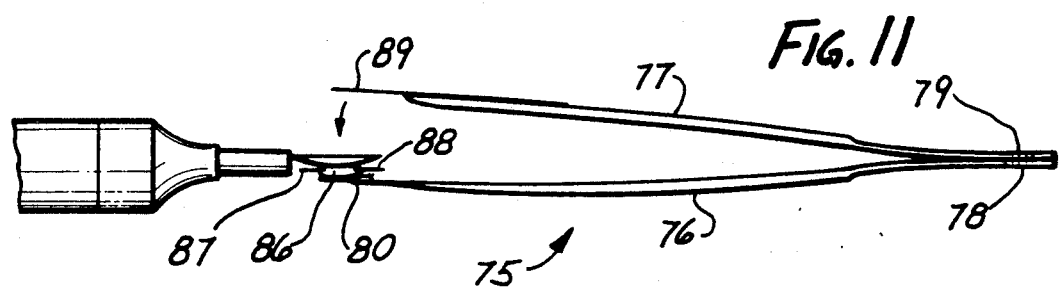
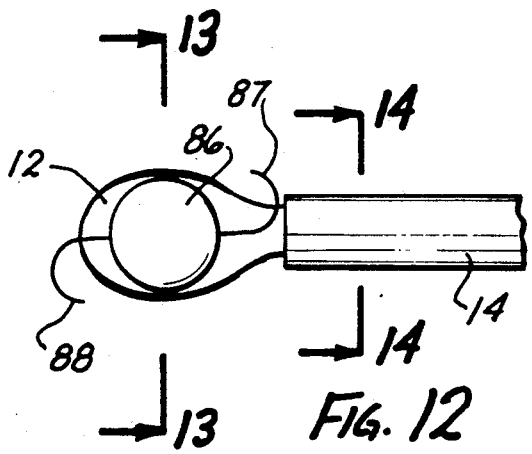
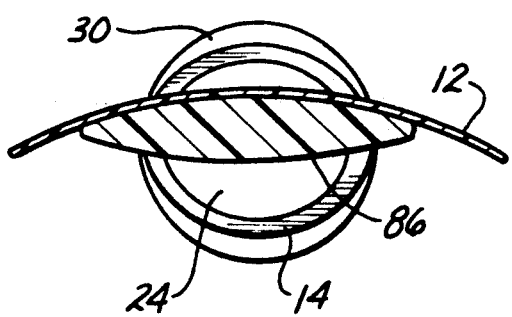
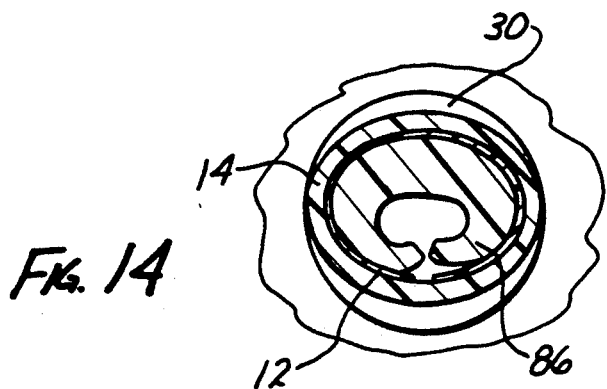

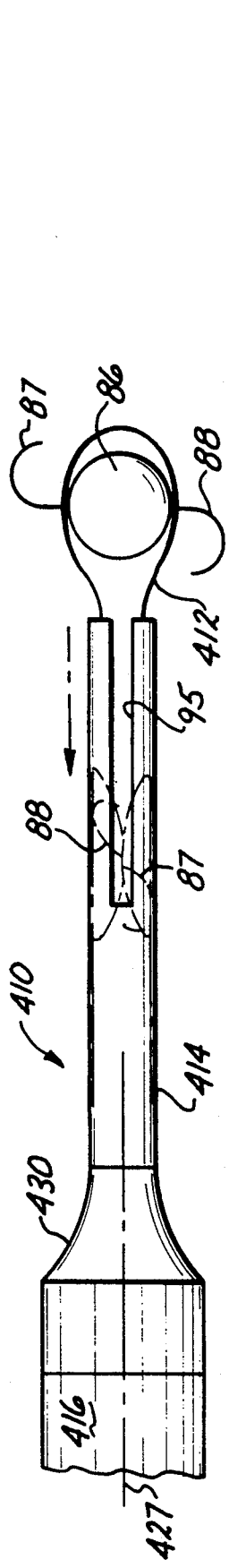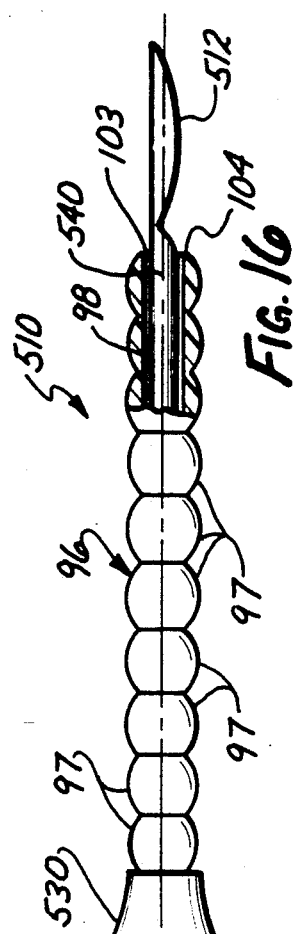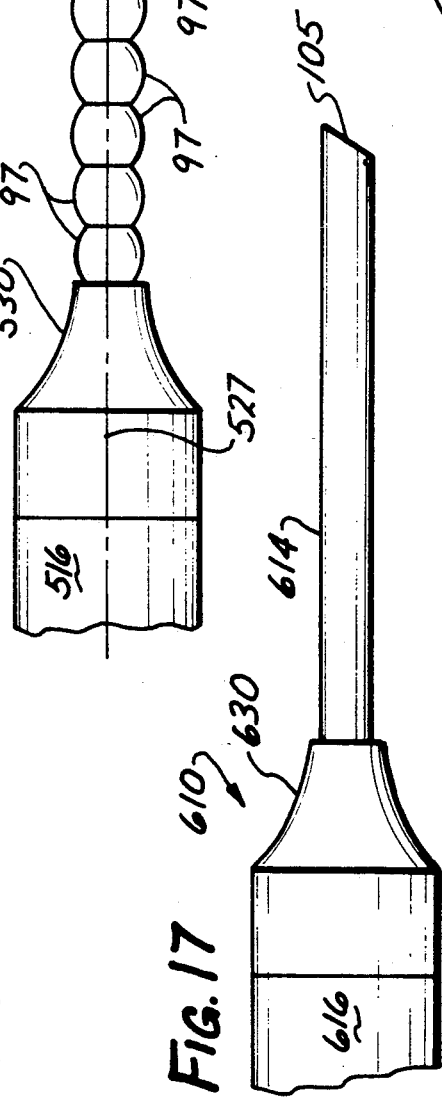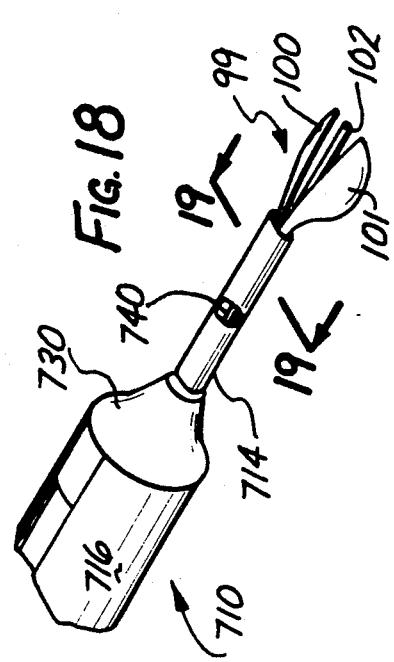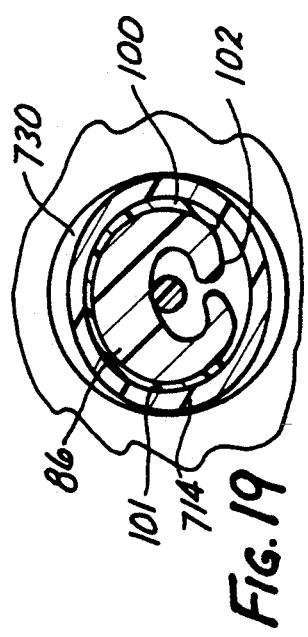

SMALL INCISION INTRAOCULAR LENS INSERTION APPARATUS

BACKGROUND OF THE INVENTION

The present invention relates to an apparatus for inserting a foldable item, e.g., a foldable intraocular lens and the like, into an eye. More particularly, the invention relates to such an apparatus constructed so as to be distally loaded with the item to be inserted.

An intraocular lens is implanted in the eye, e.g., as a replacement for the crystalline lens after cataract surgery. Intraocular lenses often include an optic, and preferably at least one flexible fixation member, e.g., a haptic, that extends from the optic and becomes affixed in the eye to secure the lens in position. The optic normally includes a transparent or optically clear optical lens. Implantation of such lenses into the eye involves making an incision in the eye. It is advantageous, e.g., to reduce trauma and speed healing, to have the incision sized as small as possible.

Intraocular lenses are known which are foldable for ease of insertion into the eye. A substantial number of instruments have been proposed to aid in inserting such a foldable lens in the eye. Many of these instruments involve pre-folding the lens before the lens is placed in the insertion device. While this hand folding allows the lens to be inserted through a relatively small incision, it is time consuming and the added handling can damage the lens.

Hauser U.S. Pat. No. 4,763,650 discloses an insertion device in which a deformable lens is grasped in its undeformed state in a pair of detachable jaws. The jaws are held stationary while a ramp and a thin walled tube are moved forward. The resulting ramping action causes the jaws to be drawn into the tube and to compress around the lens. The jaws are detached from the remainder of the device as the lens is inserted in the eye. It would be advantageous to employ a lens insertion system which did not require a ramp and/or which remains in tact throughout the lens insertion process.

Other devices, such as those described in Jampel et al U.S. Pat. No. 4,747,404 and in Baccala et al U.S. Pat. No. 4,785,810, use loading systems to fold the lens into the insertion apparatus and/or fold the lens through a longitudinally extending slot in the insertion apparatus. Such loading systems are relatively complex, while the relatively large longitudinally extending slots tend to cause problems in inserting the lens in the eye relative to using a substantially unbroken delivery tube.

SUMMARY OF THE INVENTION

A new apparatus and method useful for surgically inserting a foldable item, in particular a foldable intraocular lens, into an eye has been discovered. This system allows the use of a relatively small incision in the eye for insertion purposes. In addition, the present apparatus can be distally loaded with the item at the time of the surgery. This allows the surgeon to inspect the lens, in its unfolded state, immediately before inserting the item in the eye. Further, this distal loading of the lens is done with a minimum of handling. Thus, the item has reduced susceptibility to being damaged during the loading process. Further, the loading process is performed very speedily and reliably. The present apparatus is quite simple and can be produced in a number of forms, as will be discussed hereinafter, to suit the individual needs of the surgical application involved and/or the likes and dislikes of the surgeon. Using the present apparatus, the surgeon can easily and controllably place an item into a patient's eye, even into the capsular bag of the patient's eye.

In one broad aspect, the present invention is directed to an apparatus for inserting a foldable item, in particular a foldable intraocular lens, IOL, into an eye through an incision in the eye. This apparatus comprises a paddle means sized and adapted to contact the item in the unfolded state; elongated tube means including a distal opening, an interior space sized and adapted to receive the paddle means in contact with the item in the folded state, and movement means to provide for relative movement between the paddle means and the tube means. The elongated tube means includes a distal end portion sized and adapted to be inserted into the eye through the incision. The tube means and the paddle means cooperate to fold the item into the folded state as the item, carried by the paddle means, is received through the distal opening into the interior space. The present apparatus is usable without requiring a ramp assist, as in the above noted Hauser patent.

In one embodiment, the paddle means is permanently affixed to the apparatus. In this manner the present system is further distinguished from the Hauser patent noted above, in which the jaws of the system were detachable during the surgery.

In another particularly useful embodiment, the movement means acts to provide movement of the paddle means relative to the tube means. This embodiment provides a still further distinction from the above noted Hauser patent in which the thin wall tube and ramp are moved forward while the jaws are held stationary. In this embodiment the paddle means and the unfolded item are moved through the distal opening of the tube means into the interior space.

In an additional particularly useful embodiment, the paddle means includes a flexible element which is sized to carry the item in the unfolded state. This flexible element is adapted to be received in the interior space of the elongated tube means. Preferably, a single generally tear drop or pear-shaped flexible element is used. The generally tear drop or pear-shaped flexible element is generally rounded at its distal end and narrows toward its proximal end. This embodiment has been found especially useful in that the flexible element actually wraps around the item as it is folded. An additional advantage of such a flexible element is that when the item, in particular an IOL, includes at least one flexible fixation member, the item can be oriented with respect to the flexible element so that the fixation member is generally parallel to or perpendicular to the longitudinal axis of the elongated tube. This feature allows the surgeon substantial flexibility in inserting the item into the patient's eye. Although the flexible element may be of any suitable size, the width of the flexible element, i.e., the maximum dimension of the flexible element substantially perpendicular to the longitudinal axis of the elongated tube, is preferably in the range of about 4 mm to about 9 mm. Smaller flexible elements are particularly useful in the present small incision insertion apparatus. Also, smaller flexible elements have been found to be very effective in cooperating with the tube means to fold the item to be inserted, and are more readily controlled and positioned in the eye during the insertion procedure, relative to larger flexible elements. For example, the use of a relatively small flexible element allows an IOL to be placed in the capsular bag of the eye. Thus, the width of the flexible element is more preferably less than about 8.5 mm, and still more preferably in the range of about 5.5 mm to about 7.5 mm. Excellent results are achieved when the flexible element has a width in the range of about 6.5 mm to about 7 mm. The length of the flexible element, i.e., the maximum dimension of the flexible element substantially parallel to the longitudinal axis of the elongated tube, is preferably in the range of about 9.5 mm to about 11 mm.

The tube means may further include a slot extending proximally from the distal opening and outwardly from the interior space. This slot, which preferably extends through the tube means, is sized and adapted so that when the item, in particular an IOL, is in the interior space the flexible fixation member or members of the item extend into, and preferably protrude from, the slot. The slot is preferably not sufficiently wide to allow any portion of the foldable body of the item, e.g., the optic of an IOL, to extend into the slot. This feature reduces the chances of damaging the flexible fixation members while, at the same time, maintaining a substantially smooth and continuous outer peripheral surface of the tube means to allow for relatively easy insertion through the incision in the eye.

At least a part of the paddle means, and in particular the flexible element, is preferably transparent. This feature allows the surgeon maximum opportunity to view the item as it is being loaded into the insertion apparatus. One particularly useful class of materials from which the paddle means can be produced are polymeric materials. Especially preferred materials from which the flexible element of the paddle means can be constructed are the polyesters, in particular statically charged polyesters, for example the polyester sold by Cadillac Plastics under the trademark Mylar.

The tube means may include a distal end which is substantially perpendicular to the longitudinal axis of the tube means. However, in one embodiment it is preferred that this distal end is beveled. That is, at least a portion of this distal end is oriented at an angle other than perpendicular to the longitudinal axis of the tube means. Such beveling may be of any suitable configuration which allows for easier insertion of the tube means into the eye, relative to a tube means with an unbeveled distal end. The tube means preferably has a substantially elliptical outer cross-section perpendicular to its longitudinal axis. These features provide for increased ease in inserting the tube means through the incision in the eye.

The interior space in the tube means is preferably substantially uniform in cross sectional area (perpendicular to the longitudinal axis of the tube means) along its length. In order to provide for increased ease in loading the item into the apparatus and in inserting the item into the eye, it is preferred that the axial wall of the interior space be rifled, e.g., include one or more helical ridges.

The outer peripheral wall of the tube means may be smooth to allow for relative ease in inserting the tube through the incision in the eye. However, another factor must be considered in designing the tube means. The tube means must have sufficient strength to cooperate with the paddle means to fold the item as the item is loaded into the interior space. At the same time, the tube means must have a sufficiently small cross sectional profile (perpendicular to the longitudinal axis of the tube means) to allow the tube means to be inserted through the small incision in the eye. In one embodiment, the outer peripheral surface of the tube means is ribbed to provide additional strength to the tube means. The radial thickness of the tube means between the axial wall of the interior space and the outer peripheral surface of the tube means is preferably at least about 0.051 mm, and more preferably no greater than about 0.381 mm. Such dimension has been found to provide sufficient strength when the tube means is made of one or more metals, in particular stainless steel, such as the 300 series stainless steel, e.g., 303, 304 and 316 stainless steels. In any event, the material or materials used to construct the present insertion apparatus, and in particular those components of the present apparatus which are actually inserted into the eye, should be such as to cause no undue damage to the eye or patient being treated.

The movement means referred to above may act to move the paddle means relative to the tube means or may act to move the tube means relative to the paddle means. Thus, one surgeon may prefer to have the paddle means move relative to the tube means while another surgeon may wish to have the tube means move relative to the paddle means. The present system can be structured to operate in either one of these two modes.

Although the present movement means may be automatically operable, such feature can add costly and unnecessary sophistication to the present apparatus. For this reason, it is preferred that the movement means be manually operable. In one embodiment, the movement means includes a mechanism capable of being activated by sliding relative to the paddle means or the tube means. This mechanism may be located at or near the proximal end of the apparatus or, alternately and preferably, away from the proximal end of the apparatus. For example, the mechanism may involve a plunger type device extending from the proximal end of the apparatus and connected to either the paddle means or the tube means. Alternately and preferably, the mechanism may include a slidable stem or slider located on the side, e.g., protruding through a slot and extending outwardly from the outer peripheral wall or surface, of the housing means, in particular toward the distal end portion of the housing means, of the apparatus. This stem is connected to either the paddle means or the tube means and, by sliding along a length of the housing means, causes either the paddle means or the tube means to move.

The present invention further includes a method for inserting a foldable item into an eye. This method comprises placing the item in the unfolded state in contact with a paddle means, passing the item in contact with the paddle means through a distal opening into an interior space of a tube means, thereby folding the lens in contact with the paddle means; inserting the tube means into the eye; withdrawing the item in contact with the paddle means from the interior space through the distal opening; and withdrawing the paddle means and tube means from the eye. The item is released by or separated from the paddle means prior to the paddle means and tube means being withdrawn from the eye. The item, in its unfolded state, remains in the eye. This method can be performed, with various modifications, with the various embodiments of the insertion apparatus set forth herein. An incision is made in the eye prior to inserting the tube means into the eye. Once the tube means and paddle means are withdrawn from the eye the incision can be mended.

Another aspect of the present invention involves an apparatus and method useful for loading a foldable item, in particular a foldable IOL, for example, into the present insertion apparatus. This loading system is relatively simple, very reliable and allows for visual inspection of the item just prior to loading the item.

In one embodiment, the present loading apparatus comprises an elongated first element having a distal end portion and a proximal end portion, and an elongated second element having a distal end portion in the form of a rod element and a proximal end portion. A platform member is affixed to the first element at or near the distal end portion of the first element. This platform member has a surface sized and adapted to carry the item, in its unfolded state. The distal end portions of the first and second elements are joined together in such a manner that the distal end portions of these elements are movable toward or away from each other, e.g., in a "forceps-like" action. The loading apparatus is preferably structured to be biased to keep the distal end portions of the elements apart. This biasing is preferably overcome using manual force. The first and second elements are movable relative to each other to allow the rod element to contact the item being carried by the surface to hold the item in place on the surface. The rod element preferably has a dimension generally perpendicular to this longitudinal axis of the first element which is smaller than the maximum dimension of the surface of the platform generally perpendicular to the longitudinal axis. This feature allows the surgeon to visually inspect the item being held between the surface and the rod element.

This loading apparatus may be used to load an item into the present insertion apparatus. Thus, the item, in its unfolded state, to be loaded is placed on a surface. The item is held in place on the surface with a rod element in contact with the item. When it is desired to load the item into the insertion apparatus, the rod element is moved out of contact with the item being carried by the surface, and the paddle means of the insertion apparatus is positioned in contact with the item on the surface. The paddle means is drawn into the tube means, as described herein, and the item is ready to be inserted into the eye.

The foldable intraocular lenses insertable in the eye using the present system may be of any configuration suitable to perform the desired function in the eye. Such lenses often include a lens body or optic which has optical properties in the eye. Such lens body may have any suitable configuration, provided that it is foldable as set forth herein. In many instances the lens body is generally circular. However, other configurations are also useful. In addition, the intraocular lenses may, and preferably do, include at least one flexible fixation member which is secured or attached to the optic. This flexible fixation member acts to fix the intraocular lens in position in the eye. Examples of flexible fixation members include flexible haptics which are preferably radially resilient and extend outwardly from the periphery of the lens body. Specific examples of such flexible haptics include those commonly known as J-loops and C-loops. Such haptics engage appropriate circumferential eye tissue adjacent the iris or within the capsular bag to fix the lens in position in the eye. A very useful intraocular lens includes a plurality of, especially two, such flexible haptics.

As used herein, the terms "deformable" or "foldable" means that the item or IOL, and in particular the lens body or optic, can be temporarily reshaped so as to pass through a smaller, e.g., in terms of diameter, incision relative to the incision required if the lens was not temporarily reshaped.

The lens body may be made of any suitable material such as polymethylmethacrylate, silicone, hydrogel or other well known materials for foldable lens construction. Preferably, the lens body also includes an ultraviolet light absorber. The flexible fixation member or members may be made of any suitable material such as polymethylmethacrylate, prolene, polypropylene, nylon, silicone or other materials suitable for implantation into the eye.

These and other aspects and advantages of the present invention are set forth in the following detailed description and claims, particularly when considered in conjunction with the accompanying drawings in which like parts bear like reference numerals.

BRIEF DESCRIPTION OF DRAWINGS

FIG. 1 is a perspective view of one embodiment of the present lens insertion apparatus.

FIG. 2 is a cross-sectional view taken along line 3—3 of FIG. 1 showing the paddle fully retracted.

FIG. 3 is a fragmentary cross-sectional view taken along line 3—3 of FIG. 1.

FIG. 4 is a cross-sectional side view showing an alternate embodiment to that in FIGS. 1, 2 and 3 with the tube fully retracted.

FIG. 5 is a fragmentary cross-sectional side view showing the alternate embodiment shown in FIG. 4 with the tube fully extended.

FIG. 6 is a perspective view of another embodiment of the present lens insertion apparatus.

FIG. 7 is a cross-sectional view taken along line 7-7 of FIG. 6 showing the paddle fully retracted.

FIG. 8 is a cross-sectional side view showing a further alternate embodiment of the present lens insertion apparatus.

FIG. 9 is a diagrammatic view showing an intraocular lens being inserted into an eye in accordance with the present invention.

FIG. 10 is a perspective view of an embodiment of the present lens loading apparatus.

FIG. 11 is a fragmentary side elevation view showing the lens loading apparatus shown in FIG. 10 in use with the lens insertion apparatus shown in FIG. 1.

FIG. 12 is a fragmentary bottom view of the paddle and tube of the insertion apparatus shown in FIG. 1 showing an intraocular lens about to be drawn into the tube.

FIG. 13 is a cross-sectional view taken along line 13—13 of FIG. 12.

FIG. 14 is a cross-sectional view taken along line 14—14 of FIG. 12 after the lens is drawn into the tube.

FIG. 15 is a fragmentary bottom elevation view showing another alternate embodiment of the present lens insertion apparatus.

FIG. 16 is a fragmentary side elevation view, partly in cross-section, showing a still further alternate embodiment of the present lens insertion apparatus.

FIG. 17 is a fragmentary side elevation view showing yet another alternate embodiment of the present lens insertion apparatus.

FIG. 18 is a fragmentary perspective view showing an additional embodiment of the present lens insertion apparatus.

FIG. 19 is a cross-sectional view taken along line 19—19 in FIG. 18 after the lens has been drawn into the tube.

FIG. 20 is a cross-sectional view taken along line 20—20 of FIG. 7.

DETAILED DESCRIPTION OF THE DRAWINGS

FIGS. 1, 2 and 3 show, in general, a lens insertion apparatus 10, which includes a flexible paddle 12, a distally open hollow tube 14, a handle or housing 16, a longitudinally extending slot 18 extending to a distal end of the housing 16 as shown in FIG. 3 and an outwardly extending slider 20. Tube 14 has an open distal end 22 which defines a distal opening 23 that leads to interior space 24, partially defined by axial wall 26. Tube 14 and interior space 24 have generally elliptical cross-sections perpendicular to the longitudinal axis 27 of apparatus 10. Housing 16 is hollow with an inner space 28 defined by distal end element 30, a peripheral wall 32 and a proximal end wall 34. Tube 14 is made of 304 stainless steel and has a solid wall thickness, perpendicular to the longitudinal axis 27, of at least about 0.051 mm, in particular about 0.115 mm.

The lens insertion apparatus 10 is structured so that slider or protruding portion 20 is integral with a plug or body 36, which is sized and adapted to move axially in inner space 28. Plug 36 includes an axially extending through hole 38 into which is secured, e.g., using adhesives or other conventional means of securement, the proximal end 39 of elongated element 40. The distal end of elongated element 40 is secured to flexible paddle 12, which paddle has a generally tear drop-like configuration with a width (in the unfolded state) of about 7 mm and a length of about 10 mm and is made of transparent polyester. Tube 14 extends into an axially extending opening of the distal end element 30 (FIG. 3) and is secured to distal end element 30.

Flexible paddle 12 is movable relative to tube 14 of insertion apparatus 10 as follows. With slider 20 in a position as shown in FIG. 2, flexible paddle 12 is folded (as will be discussed hereinafter) and entirely within interior space 24 of tube 14. As slider 20 is moved distally within slot 18 toward distal end element 30, flexible paddle 12 moves (relative to tube 14) toward distal opening 23. As slider 20 is moved distally so that plug 36 contacts distal end element 30 (which contact acts as a stop to the distal movement of slider 20, as in FIG. 3), flexible paddle 12 is entirely outside interior space 24 of tube 14. When it is desired to retract flexible paddle 12 into interior space 24, slider 20 is simply moved proximally in slot 18 until flexible paddle 12 is so retracted. The proximal end 42 of slot 18 comes in contact with slider 20 as slider 20 is moved proximally and acts as a stop to such proximal movement.

An alternate lens insertion apparatus, designated as 110, is shown in FIGS. 4 and 5. Except as expressly set forth below, the apparatus 110 is structured and functions substantially similarly to apparatus 10. Components of apparatus 110 which correspond to components of apparatus 10 are given corresponding reference numerals increased by 100.

Referring now to FIGS. 4 and 5, apparatus 110 includes a stationary plug 44 which is secured in place in inner space 128. Stationary plug 44 includes an axially extending through hole 46 into which is secured the proximal end 139 of elongated element 140, which is longer than elongated element 40. In this manner flexible paddle 112 is held stationary with respect to housing 116. Slider 120 is integral with sliding plug 47 which includes a relatively large diameter, axially extending through hole 48. The proximal end of tube 114, which is longer than tube 14, is secured in hole 48, and is not secured to distal end element 130. Thus, tube 114 is movable with slider 120 relative to housing 116. To illustrate, with slider 120 positioned fully proximally in slot 118, as shown in FIG. 4, tube 114 is fully retracted and flexible paddle 112 is fully outside the interior space 124 of tube 114. By moving slider 120 distally to a position shown in FIG. 5, tube 114 moves and captures stationary flexible paddle 112 in interior space 124 through distal opening 123.

FIGS. 6, 7 and 20 illustrate another lens insertion apparatus, shown generally at 210. Except as expressly set forth below, lens insertion apparatus 210 is structured and functions substantially similarly to apparatus 10, as described herein. Components of apparatus 210 which correspond to components of apparatus 10 are given corresponding reference numerals increased by 200.

The primary difference between the two apparatus 10 and 210 is in the structure to move the flexible paddle relative to the tube. In apparatus 210, a proximally open housing 49 is provided which includes a peripheral wall 50 secured at its distal end to distal end element 230. Peripheral wall 50, together with distal end element 230, defines inner space 51. Finger rings 52 and 53 extend radially from opposing sides of peripheral wall 50. A plunger element 54 is slidably fitted into inner space 51 and extends proximally of housing 49. The proximal end of plunger element 54 is provided with a radially extending thumb ring 55, which facilitates manually moving, e.g., using only one hand, plunger element 54 in and out of inner space 51, as desired. The distal end of plunger element 54 includes an axially extending hole 56 into which is secured the proximal end of elongated element 240. One additional feature of apparatus 210 is axial wall 57 of tube 214. Axial wall 57 is rifled, as illustrated in FIG. 20, to provide for ease in moving paddle 212 relative to tube 214.

Plunger element 54 is pulled proximally of housing 49, as shown in FIG. 7 to retract flexible paddle 212 into interior space 224. By pushing plunger element 54 distally, flexible paddle 212 extends fully out of distal opening 223 of tube 214. As plunger element 54 is moved distally relative to housing 49, plunger element 54 comes into contact with distal end element 230 and acts as a stop to this distal movement.

FIG. 8 illustrates a further alternate lens insertion apparatus, shown generally at 310. Except as expressly set forth below, lens insertion apparatus 310 is structured and functions substantially similarly to apparatus 210. Components of apparatus 310 which correspond to components of apparatus 210 are given corresponding reference numerals increased by 100.

The primary difference between the two apparatus 210 and 310 is that in apparatus 210 the flexible paddle 212 is movable and the tube 214 is stationary relative to housing 49, whereas in apparatus 310 the tube 314 is movable and the flexible paddle 312 is stationary relative to housing 60. Apparatus 310 has an elongated housing 60 including a peripheral wall 61. An axially extending inner space 62 is defined by distal end element 330, peripheral wall 61 and the proximal end wall 63 of housing 60. Two axially extending slots 64 and 65 are positioned in opposing sides of peripheral wall 61. A stationary plug 66 is secured in to peripheral wall 61 toward the proximal end of inner space 62. Stationary plug 66 includes an axially extending through hole 67 into which is secured the proximal end of elongated element 340, which is longer than elongated element 240. In this manner, paddle 312 is held stationary relative to housing 60.

A slidable plug 68 is positioned in inner space 62, and includes a relatively large axially extending through hole 69 and two radially extending finger rings 70 and 71 which extend out of slots 64 and 65, respectively. The proximal end of tube 314 is secured in hole 69. Tube 314 is longer than tube 214 and is not secured to distal end portion 330. A thumb ring 72 is secured to, and extends proximally from, proximal end wall 63. As shown in FIG. 8, finger rings 70 and 71 and thumb ring 72 are substantially coplanar. Finger rings 70 and 71 and thumb ring 72 facilitate manually moving, e.g., using only one hand, slidable plug 68 (and tube 314) relative to housing 60 (and flexible paddle 312).

As shown in FIG. 8, slidable plug 68 is moved to the distal end of slots 64 and 65 where its movement is stopped. In this configuration, paddle 312 is totally within interior space 324 of tube 314. As slidable plug 68 is moved toward the proximal ends of slots 64 and 65, where its movement is again stopped, tube 314 retracts and paddle 312 passes through distal opening 323 and is totally outside interior space 324.

Before describing in detail the functioning of the insertion apparatus shown in FIGS. 1 to 8, reference is made to a lens loading apparatus, shown generally as 75, in FIG. 10. Loading apparatus 75 is a forceps-like arrangement including a first elongated element 76 and a second elongated element 77, which are joined together at their respective proximal ends 78 and 79. The distal end of first element 76 includes a planar surface 80 which is oriented to be substantially flat when apparatus 75 is laid on a flat surface with only first element 76 touching this flat surface. Planar surface 80 is sized and adapted to carry foldable intraocular lens 85, which includes optic 86 and first and second flexible haptics 87 and 88. A relatively narrow, rod-like extension 89 is secured to second element 77 and extends distally of second element 77. Extension 89 is more narrow (in a direction perpendicular to planar surface 80 and to the longitudinal axis 81 of first element 76) than planar surface 80 to allow visual inspection of lens 85 as it is held on planar surface 80 by extension 89.

The general functioning of loading apparatus 75 is described with reference to the insertion apparatus 10, in FIGS. 1, 2 and 3. However, it will be apparent that such loading apparatus 75 may be used in a substantially similar manner with each of the other insertion apparatus described herein, and all such uses are within the scope of the present invention.

Referring now to FIGS. 10, 11, 12, 13 and 14, loading device 75 functions as follows. The intraocular lens 85 is positioned with optic 86 on planar surface 80 and the first and second haptics 87 and 88 oriented substantially parallel to the longitudinal axis of the first element 76. If desired, intraocular lens 85 can be positioned so that first and second haptics 87 and 88 are oriented substantially perpendicular to the longitudinal axis 81 of the first element 76. First and second elements 76 and 77 are squeezed together so that extension 89 comes into contact with optic 86. In this manner lens 85 is secured against movement.

With lens 85 held between planar surface 80 and extension 89, the surgeon may visually inspect that the lens is properly oriented. After such inspection, extension 89 is moved out of contact with lens 85 and insertion apparatus 10 is positioned so that the flexible paddle 12 is on top of and in contact with lens 85 carried by planar surface 80, as shown in FIG. 11. FIGS. 12 and 13 show the positioning of lens 85 relative to paddle 12 as in FIG. 11, without showing planar surface 80.

As slider 20 is moved toward the proximal end 42 of slot 18, paddle 12 and lens 85 move through distal opening 23 of tube 14 into interior space 24. As this movement occurs, paddle 12 and tube 14 cooperate to fold optic 86 so that when both paddle 12 and optic 86 are entirely in interior space 24, optic 86 is as shown in FIG. 14. In this position, lens 85 is loaded into insertion apparatus 10 and loading apparatus 75 has performed its function.

Referring now to FIG. 9, insertion apparatus 10 functions as follows. The lens 85 is to be placed in eye 92 into an area formerly occupied by the natural lens of the eye. FIG. 9 shows the sclera 93 of the eye 92 having an incision through which the distal portion of insertion apparatus 10 may be inserted. Specifically, with paddle 12 and optic 86 entirely within interior space 24, as shown in FIG. 14, an incision is made in sclera 93 and the distal end of tube 14 is inserted into this incision. The tube 14 is manipulated within eye 92 until it is positioned so that lens 85 can be properly positioned in eye 92, e.g., in the anterior chamber, the posterior chamber, the capsular bag 94, or in the sulcus, after being released from paddle 12. Thus, the surgeon is able to controllably position tube 14 before releasing lens 85. Also, since slider 20 is movable only a limited distance distally, the surgeon is able to precisely place the lens 85 without concern for "over shooting" the target area. Once tube 14 is so positioned, slider 20 is moved distally in slot 18 so that paddle 12 and optic 86 pass out of interior space 24 through distal opening 22. As paddle 12 and optic 86 unfold, lens 85 separates from, or is released by, paddle 12 and remains in eye 92. The relatively small size of flexible paddle 12 provides for increased flexibility in positioning lens 85 in eye 92. In other words, relatively small flexible paddle 12 is able to be passed into various positions in eye 92, e.g., in or near capsular bag 94, which are not practical or even possible using a bigger paddle. After flexible paddle 12 is retracted into tube 14, insertion apparatus 10 is withdrawn from the eye 92. If needed, the position of lens 85 can be adjusted by a small, bent needle, or similar tool inserted into the same incision.

Once the lens 85 is properly placed in eye 92 and insertion apparatus 10 is withdrawn from eye 92, the incision in the sclera 93 is mended, e.g., using conventional techniques. After use, insertion apparatus 10 is preferably disposed of.

Insertion apparatus 110, 210 and 310 function in a manner substantially similar to that described with regard to insertion apparatus 10. One difference is that paddle 12 is movable relative to housing 16 in apparatus 10, whereas in apparatus 110 and 310 tubes 114 and 314 are movable relative to housings 116 and 60, respectively. Also, in apparatus 210, paddle 212 is moved by moving plunger element 54 proximally or distally relative to housing 49, while in apparatus 310, tube 314 is moved by moving slidable plug 68 proximally or distally in slots 64 and 65.

Referring now to FIG. 15, another alternate lens insertion apparatus is shown generally at 410. Except as expressly set forth below, lens insertion apparatus 410 is structured and functions substantially similarly to apparatus 10. Components of apparatus 410 which correspond to components of apparatus 10 are given corresponding reference numerals increased by 400.

The primary difference between apparatus 410 and apparatus 10 is that tube 414 includes a single distally open, axially extending through slot 95. Apparatus 410 is particularly applicable when it is desired to orient lens 85 relative to paddle 412 so that the haptics 87 and 88 are generally perpendicular to the longitudinal axis 427 of apparatus 410, as shown in FIG. 15. As lens 85 is drawn into the interior space of tube 414, optic 86 is folded and haptics 87 and 88 extend into and protrude out of slot 95. Slot 95 is wide enough to allow haptics to extend into and protrude from it, while being sufficiently narrow so as not to substantially disrupt the outer surface of the tube 414. This relatively narrow through slot 95 allows the tube 414 to be easily inserted into the eye 92 while still protecting the haptics 87 and 88 from damage.

Referring now to FIG. 16, a still further alternate lens insertion apparatus shown generally at 510. Except as expressly set forth below, lens insertion apparatus 510 is structured and functions substantially similarly to apparatus 10. Components of apparatus 510 which correspond to components of apparatus 10 are given corresponding reference numerals increased by 500.

The primary difference between apparatus 510 and apparatus 10 is the substitution of ribbed tube 96 for tube 14. Ribbed tube 96 is made of a polymeric material while tube 14 is made of stainless steel. Ribbed tube 96 includes a series of strength enhancing ribs 97. The wall thickness (perpendicular to the longitudinal axis 527) ranges from 0.128 mm to 0.256 mm. Ribbed tube 96 is sufficiently strong to cooperate, without structural failure, with paddle 512 to fold optic 86 as the optic is drawn through distal opening 103 in distal end 104 of ribbed tube 96 into the interior space 98 of ribbed tube 96. Interior space 98 and ribbed tube 96 have generally elliptical cross-sections perpendicular to longitudinal axis 527. The ribbed tube allows relatively low strength polymeric materials to be used as tube construction materials.

Referring now to FIG. 17, yet another alternate lens insertion apparatus is shown generally at 610. Except as expressly set forth below, lens insertion apparatus 610 is structured and functions substantially similarly to apparatus 10. Components of apparatus 610 which correspond to components of apparatus 10 are given corresponding reference numerals increased by 600.

The primary difference between apparatus 610 and apparatus 10 is that the distal end 105 of tube 614 is beveled. This facilitates and/or makes easier the insertion of tube 614 into the eye.

Referring now to FIGS. 18 and 19, an additional lens insertion apparatus is shown generally at 710. Except as expressly set forth below, lens insertion apparatus 710 is structured and functions substantially similarly to apparatus 10. Components of apparatus 710 which correspond to components of apparatus 10 are given corresponding reference numerals increased by 700.

The primary difference between apparatus 710 and apparatus 10 is that flexible paddle 12 is replaced by a folding assembly, shown generally as 99. Folding assembly 99 includes a first flexible element 100, a second flexible element 101 and a rod element 102, each of which is secured to elongated element 740. First and second flexible elements 100 and 101 are transparent and can be made of materials from which flexible paddle 12 is made. Folding assembly 99 is structured so that each of the first and second flexible elements 100 and 101 and the rod element 102 separate, as shown in FIG. 18, when folding assembly 99 extends distally from tube 714.

With folding assembly 99 positioned as shown in FIG. 18, lens 85 is placed (e.g., using loading apparatus 75) between first and second flexible elements 100 and 101 and rod element 102. Folding assembly 99 is then drawn into tube 714. This causes tube 714 and folding assembly 99 to cooperate to fold optic 86, as shown in FIG. 19. With lens 85 loaded in apparatus 710, tube 714 is inserted into an incision in the eye and elongated element 740 is moved distally to move folding assembly 99 out of tube 714. This causes lens 85 to be released from apparatus 710, which can then be removed from the eye.

The various individual features illustrated in one or more specific embodiments described herein can be used alone or together in other embodiments and all such other embodiments are within the scope of the present invention.

While this invention has been described with respect to various specific examples and embodiments, it is to be understood that the invention is not limited thereto and that it can be variously practiced within the scope of the following claims.

What is claimed is:

1. An apparatus for inserting a foldable intraocular lens into an eye comprising:
    a handle including a peripheral wall and an end element attached to the peripheral wall adjacent one end of the peripheral wall, said handle having an elongated chamber, said end element having an axially extending opening extending through the end element;
    a tube having an axially extending passage extending through the tube;
    a portion of said tube being received in the axially extending opening of the end element;
    means for attaching the tube to the end element with said portion of the tube being in said axially extending opening of the end element;
    said peripheral wall having a distal end and a slot in the peripheral wall leading to said chamber and extending to the distal end;
    an actuator having a body movable longitudinally in said chamber and a protruding portion which extends from the body through the slot, the protruding portion and the body being unitary;
    a flexible paddle; and
    an elongated element extending through the passage of the tube and coupling the paddle to the actuator.

2. An apparatus as defined in claim 1 wherein the tube has a tube wall defining the passage of the tube and the thickness of the tube wall is a least about 0.051 mm and no greater than about 0.381 mm.

3. An apparatus as defined in claim 1 wherein the tube is metal.

4. The apparatus of claim 3 wherein said metal is stainless steel.

5. The apparatus of claim 3 wherein said metal is selected from the group consisting of the 300 series stainless steels.

6. The apparatus of claim 1 wherein said tube further includes a distal end which is beveled.

7. The apparatus of claim 1 wherein said tube has an axial wall which is rifled.

8. The apparatus of claim 1 wherein said tube has a substantially elliptical cross-section perpendicular to the longitudinal axis of said apparatus.

9. The apparatus of claim 1 wherein said paddle has a width in the range of about 4 mm to about 9 mm.

10. The apparatus of claim 9 wherein said paddle has a length in the range of about 9.5 mm to about 11 mm.

11. The apparatus of claim 1 wherein said paddle includes a plurality of elements which come into closer relation to each other as said paddle is received by said tube.

12. The apparatus of claim 1 wherein at least a part of said paddle is transparent.

13. A method comprising:

supporting an intraocular lens on a supporting surface;

positioning a lens insertion apparatus having a flexible paddle with the paddle being above the intraocular lens; and with the paddle above the intraocular lens, retracting the flexible paddle within a tube of the lens insertion apparatus to fold the paddle about the intraocular lens to fold the intraocular lens and to retract the intraocular lens into the tube.

14. A method as defined in claim 13 wherein said step of supporting is carried out with forceps.

15. A method as defined in claim 13 including inserting the tube through an incision into the eye and advancing the paddle out of the tube to insert the foldable lens into the eye.

* * * * *